United States Patent [19]

Cartier et al.

[11] 4,013,702
[45] Mar. 22, 1977

[54] PROCESS FOR THE PURIFICATION OF POLYCARBONATES

[75] Inventors: Jean-Pierre L. Cartier, Evry; Jean-Pierre G. Senet, Vaux le Penil, both of France

[73] Assignee: Societe Nationale des Poudres et Explosifs, France

[22] Filed: Dec. 4, 1975

[21] Appl. No.: 637,760

[30] Foreign Application Priority Data

Dec. 11, 1974 France .............................. 74.40836

[52] U.S. Cl. ........................... 260/463; 260/47 XA
[51] Int. Cl.$^2$ ........................................ C07C 68/08
[58] Field of Search ...................... 260/47 XA, 463

[56] References Cited

UNITED STATES PATENTS

| | | | |
|---|---|---|---|
| 3,213,060 | 10/1965 | Jackson et al. | 260/463 |
| 3,470,133 | 9/1969 | Ohme | 260/47 XA |
| 3,668,181 | 6/1972 | Oxenrider | 260/47 XA |

FOREIGN PATENTS OR APPLICATIONS

| | | | |
|---|---|---|---|
| 1,234,900 | 10/1960 | France | 260/463 |

*Primary Examiner*—Lewis Gotts
*Assistant Examiner*—D. R. Phillips
*Attorney, Agent, or Firm*—Bucknam and Archer

[57] ABSTRACT

The free and bonded residual phenol content of oligocarbonates prepared by transesterification between a diol and a diphenyl carbonate is substantially reduced by a process comprising (i) introducing water into the oligocarbonate in the liquid state at an elevated temperature under reduced pressure and (ii) purging the mixture with an inert gas to effect degassing. The purified oligocarbonates are particularly resistant to yellowing.

13 Claims, No Drawings

PROCESS FOR THE PURIFICATION OF POLYCARBONATES

The present invention is concerned with a process for the purification of polycarbonates and, more particularly, with a process which enables the free or bonded residual phenol content of oligocarbonates, particularly hydroxytelechelate oligocarbonates, prepared by poly-transesterification between a diol and diphenyl carbonate, to be considerably reduced.

It has been known for a long time that oligocarbonates, and particularly hydroxytelechelate oligocarbonates, can be prepared by polytransesterification between a diol and diphenyl carbonate. For example, for a hydroxytelechelate oligocarbonate, the equation is as follows:

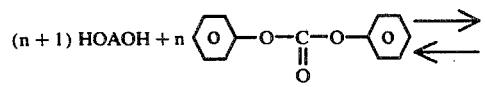

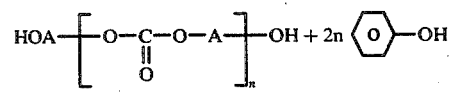

(I)

The reaction is carried out at atmospheric pressure or, preferably, under reduced pressure in order to reduce the temperature required; the phenol formed is removed from the reaction medium by distillation.

The transesterification is accompanied by side-reactions, one of the most objectionable of which is the formation of alkyl phenyl ethers, as follows:

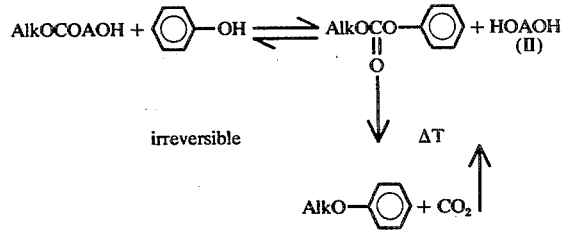

(II)

The crude product obtained thus contains both free phenol and bonded phenol in the form of alkyl phenyl ethers or alkyl phenyl carbonates.

Ultra-violet spectroscopy enables the proportion of phenoxy groups

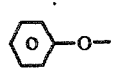

("total phenol", corresponding to the sum of the free phenol and the bonded phenol) in the oligomer to be ascertained without difficulty.

The presence of phenol in the free or bonded form in polycarbonates is objectionable, in general terms, because the purity of the final product and its reactivity are reduced thereby, and in the case of hydroxytelechelate oligocarbonates, the presence of such impurities is particularly undesirable. In order to prepare satisfactory products which can be readily used in the preparation of polyurethanes by polyaddition with diisocyanates, the total phenol should be as low as possible. If it is too high, and particularly if it is more than 0.2% by weight, the oligocarbonates possess the following disadvantages: an insufficient average number of functional groups; sensitivity to light and to oxidation, manifesting itself in an increase in coloration; an unpleasant odour; they require very careful processing by virtue of the considerable and abnormal increase in the viscosity immediately after the addition of the diisocyanate; and the polyurethanes derived therefrom have somewhat unsatisfactory mechanical properties.

The previously known processes for the production of polycarbonates which comprise carrying out the transesterification at atmospheric pressure lead to oligomers in which the free or bonded phenol content is as much as and even exceeds 0.5% by weight.

One approach to the purification of polycarbonates after transesterification is based on washing the polycarbonate with water, the polycarbonate being dissolved in a suitable solvent. Such a technique is described in French Pat. No. 1,234,900 which describes the washing of polycarbonates with hot water, the polycarbonates being dissolved in methylene chloride. The pressure is immaterial in this process. The patent does not indicate the final total phenol content of the polycarbonate, but the process described possesses a very great disadvantage: the purified polycarbonate is collected in the form of flakes floating on the surface of a tank filled with water. These flakes are very wet and rather complicated special equipment (an extrusion screw which operates under hot conditions and in vacuo) is necessary in order to obtain a final product which is dry and dense. The complexity of this technique considerably reduces its industrial value.

Another approach to reducing the phenol content of polycarbonates is based on flushing the molten polymer with an inert gas for several hours at a high temperature (180°–200° C) and under reduced pressure. It is found that although the free phenol content is effectively reduced, the total phenol remains substantially constant. Because of the high viscosity of the polycarbonates the evaporation of the free phenol is very slow and the latter reacts in accordance with equation (II).

It is obviously possible to accelerate the removal of phenol by increasing the surface area available for evaporation, for example by using a thin film evaporator. However, such apparatus is extremely expensive when it is desired to treat large amounts of material.

French Pat. No. 2,037,283 describes a process for effecting transesterification under reduced and variable pressure which, by a suitable choice of reaction conditions, enables the total phenol content to be reduced to less than 0.15%. This process, however, has the disadvantage of taking an excessively long time (on average more than 50 hours) and this seriously restricts its industrial value.

We have now found that the introduction of water, in the liquid form, into an oligocarbonate, particularly a hydroxytelechelate oligocarbonate, which is at an elevated temperature and under reduced pressure so that the oligomer is in the liquid state, is effective in considerably reducing the free phenol content and, surprisingly, the bonded phenol content. It is no less surprising to find that the polymer chain is only very slightly effected by such a treatment and that, in particular, the carbonate groups are not hydrolysed.

According to the present invention, therefore, there is provided a process for the purification of oligocarbonates formed by transesterification between a diol and a diphenylcarbonate, which comprises introducing liquid water into the oligocarbonate which is at an elevated temperature and under a reduced pressure such that the oligocarbonate is in the liquid state and, after introducing the water, flushing the liquid mixture with an inert gas, whilst maintaining the temperature and further reducing the pressure, in order to effect degassing.

The temperature of the molten oligomer is preferably from 150° to 200° C and, more preferably, from 160° to 190° C, and the pressure is preferably not more than 250 mm Hg. The water, which is preferably introduced continuously, is vaporised immediately, entraining phenol as shown by analysis of the condensates at the outlet from the reactor. The amount of water used is preferably at least ten times the total weight of the free and bonded phenol and, preferably, approximately twenty times this quantity. The water used is preferably distilled water which does not contain any dissolved oxygen.

When the transesterification reaction is carried out in the presence of basic catalysts, it is preferred to use water which has been acidified with an inorganic acid. In this case, the volume of aqueous acid solution used is preferably at least 30 ml per kg of oligomer and, preferably, approximately 60 ml per kg. The acidified water is, as before, preferably introduced continuously.

Solutions of hydrochloric acid or phosphoric acid are suitable, but sulphuric acid solutions are preferred because the neutralisation residues (alkali metal sulphates) are not particularly objectionable.

The concentration of acid is preferably such that the total amount of acidic solution introduced into the reactor is slightly greater than that necessary to neutralise the catalyst.

The treatment with water, which in substantially all cases takes less than one hour, is followed by flushing with an inert gas, preferably nitrogen or carbon dioxide, whilst maintaining the temperature and at a somewhat further reduced pressure, to effect degassing. Degassing, which is usually effected for approximately one hour, is intended to reduce the water content of the product.

The procedure in which water alone (i.e. without acid) is used, enables purified products having a total phenol content of not more than 0.15% by weight to be obtained; when this procedure is applied to hydroxytelechelate oligomers, it does not affect the proportion of hydroxyl groups in the product. The procedure using acidified water, which is simpler to carry out, enables products having a total phenol content of not more than 0.2% by weight to be obtained. The two procedures are, therefore, comparable from the point of view of effectiveness with respect to the removal of phenol, but in the case of hydroxytelechelate oligomers, it is found that the second procedure slightly affects the proportion of hydroxyl groups in the product; the first procedure is thus preferred in the case of hydroxytelechelate oligomers.

The process according to the invention can be applied to oligocarbonates having a number average molecular weight of from 1,000 to 3,000 and is, in particular, advantageously applied to oligomers derived from diols of the formula HO — A — OH, in which A is:

—$(CH_2)_p$- with $4 \leq p \leq 12$,

—$(CH_2)_2$-O-$(CH_2)_2$—,

—$(CH_2)_2$-O-$(CH_2)_2$-O-$(CH_2)_2$—,

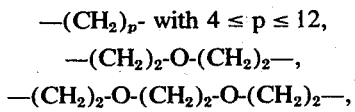

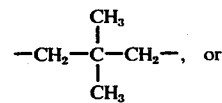

The oligocarbonates purified by the process according to the invention are particularly valuable because they are non-toxic by virtue of their very low phenol content and they are very resistant to yellowing.

In order that the invention may be more fully understood, the following examples are given by way of illustration only. All percentages are by weight unless otherwise indicated.

EXAMPLES 1 and 2

300 g of the oligocarbonate to be treated were introduced into a 1 liter reactor equipped with a stirrer, a thermometer, a manometer, a dip tube and an outlet connected to a vacuum pump equipped with a pressure regulator. The mass was heated rapidly to 180° C under 20 mm Hg, and liquid water was introduced, in portions, whilst maintaining the stated temperature and the pressure.

After the treatment with water, the pressure was reduced to 8 mm Hg and gentle flushing with nitrogen was effected for one hour, the temperature still being kept at 180° C.

The product resulting from this operation was collected and analysed. Two runs were carried out, one (Example 1) with a polycarbonate derived from hexane-1,6-diol:

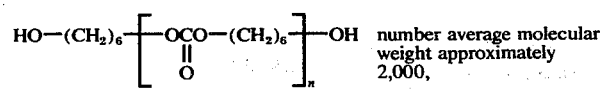

the other (Example 2) with a polycarbonate derived from diethylene glycol:

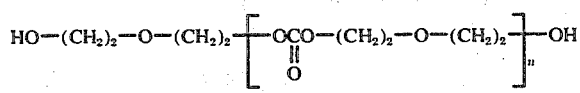

number average molecular weight approximately 2,600.

The characteristics of the original oligomers, the amounts of distilled water used and the results obtained are given in the following table:

| POLYCARBONATE | Example 1 | | Example 2 | |
|---|---|---|---|---|
| | Derived from hexane-1,6-diol Mn ≃ 2,000 | | Derived from diethylene glycol Mn ≃ 2,600 | |
| Weight of water used | 18g | | 27g | |
| | Original product | Treated product | Original product | Treated product |
| Hydroxyl content equivalent/kg | 0.98 | 0.86 | 0.76 | 0.68 |
| Water content % | — | 0.09 | — | 0.11 |
| Total phenol (free and bonded phenol content %) | 0.32 | 0.15 | 0.49 | 0.07 |
| Free phenol content % | 0.11 | 0.01 | 0.30 | 0.05 |

By way of comparison, a sample of the original oligocarbonate used in Example 1 was flushed with anhydrous nitrogen for 3 hours at 180° C under 10 mm Hg. Despite this treatment, the total phenol remained slightly more than 0.3%.

EXAMPLE 3

3.280 kg of butane-1,4-diol (purity 97%), 3.436 kg of hexane-1,6-diol (purity 98%), 12.808 kg of distilled diphenyl carbonate (purity 100%), and 300 mg of sodium methylate were introduced into a 20 liter reactor heated by a thermostatically controlled oil bath and equipped with an anchor stirrer, a packed distillation column, and a valve in the bottom.

The mixture was heated to 150° C under 100 mm Hg. After three hours, approximately 9 kg of phenol were collected. The pressure was then reduced to 10 mm Hg over the course of one hour and the temperature was then raised to 180°–185° C. This temperature was maintained until phenol ceased to be evolved. The total duration of the transesterification was 5 hours.

0.5 liter of a 1.4 × 10⁻² N aqueous solution of sulphuric acid was introduced over the course of 40 minutes, via the valve in the bottom of the reactor whilst maintaining the temperature at 180° C and under a pressure of 40 to 60 mm Hg.

After this treatment, the pressure was reduced to 10–15 mm Hg flushing with carbon dioxide (500 l/hour) was effected for one hour.

Characteristics of the oligocarbonate obtained:

| | |
|---|---|
| hydroxyl content: | 0.83 equivalent/kg |
| acidity: | < 0.01 equivalent/kg |
| water content: | 0.02% |
| free phenol content: | 0.01% |
| bonded phenol content: | 0.09% |

By way of comparison, if instead of the above treatment, the basic catalyst is simply neutralised by adding hydrogen chloride gas and the mixture is then flushed with an inert gas under the conditions indicated above, the free phenol content of the product is from 0.1 to 0.2% and the bonded phenol content is about 0.2%.

EXAMPLE 4

18.315 kg of butane-1,4-diol (purity 97%), 19.175 kg of hexane-1,6-diol (purity 98%) and 71.517 kg of diphenyl carbonate (purity 100%) were introduced into a 100 liter reactor equipped with a turbine for stirring.

The mixture was degassed in vacuo (20 mm Hg) at 120° C for 3 hours.

The pressure was then allowed to return to 760 mm Hg by introducing dry nitrogen, and 1.5 g of sodium methylate were introduced. The pressure was then reduced to 100 mm Hg and the temperature raised to 150° C. The phenol then began to distil.

These conditions were maintained for approximately two hours. The pressure was then gradually reduced to 5 mm Hg, whilst the reaction mixture was heated to 180° C; the duration of this operation was approximately one hour. The pressure was then raised to atmospheric pressure by injecting dry nitrogen and the catalyst was neutralised by the addition of 20 g of azelayl dichloride; the reaction mixture was maintained at 180° C and stirred for approximately half an hour.

The purification of the polycarbonate was then effected as follows. 5 liters of distilled water were introduced, by means of a dip tube to a point below the turbine, over the course of 1 hour, the reaction mixture being at 160° C and under a pressure of 200 mm Hg. The majority of the phenol present was entrained in the form of a water/phenol azeotrope. When this operation was complete, the pressure was reduced to 5 mm Hg whilst keeping the temperature at 180° C, and dry nitrogen was then introduced, very slowly, by means of the dip tube; the pressure thus rose again to approximately 20 mm Hg and degassing was continued for approximately one hour. The vacuum was then broken and the polycarbonate obtained was run out. A polycarbonate having the following characteristics was thus obtained:

| | |
|---|---|
| hydroxyl group content: | 1.12 equivalent/kg |
| water content: | < 0.1% |
| total phenol content: | 0.11% |
| free phenol content: | 0.02% |

What is claimed is:

1. A process for purification of an oligocarbonate formed by transesterification between a diol and a diphenylcarbonate, which comprises the steps of
   i. introducing liquid water into the oligocarbonate which is at an elevated temperature of between 150° and 200° C and under a reduced pressure not in excess of 250 mm Hg such that the oligocarbonate is in the liquid state, and (ii) flushing the mixture with an inert gas whilst maintaining the temperature and further reducing the pressure whereby degassing is effected.

2. The process according to claim 1 wherein said oligocarbonate is obtained in dry and dense form.

3. The process set forth in claim 1, wherein said oligocarbonate is maintained at a temperature of from about 160° to about 190° C.

4. The process set forth in claim 1, wherein said inert gas is selected from the group consisting of nitrogen and carbon dioxide.

5. The process set forth in claim 1, wherein the amount of water introduced is at least ten times the total weight of free and bonded phenol present in said oligocarbonate.

6. The process set forth in claim 1, wherein the amount of water introduced is about twenty times the total weight of free and bonded phenol present in said oligocarbonate.

7. The process set forth in claim 1, wherein the water introduced is acidified with an inorganic acid.

8. The process set forth in claim 7, wherein said inorganic acid is selected from the group consisting of hydrochloric acid, phosphoric acid and sulphuric acid.

9. The process set forth in claim 7, wherein the volume of aqueous acid solution introduced is at least about 30 ml per kg of said oligocarbonate.

10. The process set forth in claim 7, wherein the volume of aqueous acid solution introduced is about 60 ml per kg of said oligocarbonate.

11. The process set forth in claim 7, wherein a basic catalyst is used for the transesterification step and the concentration of acid in the aqueous acid solution is such that the total amount of acid introduced is slightly greater than that necessary to neutralise the transesterification catalyst.

12. The process set forth in claim 1, wherein the water is introduced continuously.

13. The process set forth in claim 1, wherein the water employed is distilled water which is free of dissolved oxygen.

* * * * *